United States Patent
Brotslaw et al.

(10) Patent No.: US 11,766,008 B2
(45) Date of Patent: Sep. 26, 2023

(54) CARROT VARIETY PURPLE ROYALE

(71) Applicant: SENSIENT COLORS, LLC, St. Louis, MO (US)

(72) Inventors: Daniel Jeffrey Brotslaw, Modesto, CA (US); Joerg Meyer, St. Charles, MO (US); Bradley Katsu Kaji, Livingston, CA (US)

(73) Assignee: SENSIENT COLORS LLC, St. Louis, MO (US)

( * ) Notice: Subject to any disclaimer, the term of this patent is extended or adjusted under 35 U.S.C. 154(b) by 0 days.

(21) Appl. No.: 17/716,782

(22) Filed: Apr. 8, 2022

(65) Prior Publication Data

US 2022/0330508 A1  Oct. 20, 2022

Related U.S. Application Data

(63) Continuation of application No. 16/570,588, filed on Sep. 13, 2019, now abandoned.

(60) Provisional application No. 62/794,230, filed on Jan. 18, 2019.

(51) Int. Cl.
*A01H 5/10* (2018.01)
*A01H 6/68* (2018.01)
*A01H 6/06* (2018.01)
*A01H 5/06* (2018.01)

(52) U.S. Cl.
CPC ............... *A01H 6/068* (2018.05); *A01H 5/06* (2013.01)

(58) Field of Classification Search
None
See application file for complete search history.

(56) References Cited

U.S. PATENT DOCUMENTS

2014/0245471 A1   8/2014  Freeman

*Primary Examiner* — Medina A Ibrahim
(74) *Attorney, Agent, or Firm* — QUARLES & BRADY LLP

(57) ABSTRACT

The invention relates to the carrot variety designated Purple Royale. Provided by the invention are the seeds, plants, and derivatives of the carrot variety Purple Royale. Also provided by the invention are tissue cultures of the carrot variety Purple Royale and the plants regenerated therefrom. Still further provided by the invention are methods for producing carrot plants by crossing the carrot variety Purple Royale with itself or another carrot variety and plants produced by such methods.

13 Claims, 2 Drawing Sheets
(2 of 2 Drawing Sheet(s) Filed in Color)

CARROT VARIETY PURPLE ROYALE

This application is a continuation of U.S. application Ser. No. 16/570,588 filed Sep. 13, 2019, which claims the benefit of priority of U.S. Provisional Application No. 62/794,230, filed Jan. 18, 2019, both of which are hereby incorporated by reference as if written herein in their entireties.

FIELD OF THE INVENTION

The present invention relates to the field of plant breeding. In particular, the invention provides carrot plants with a high anthocyanin level in the roots. The invention further provides fora new and distinct carrot variety designated Purple Royale and for breeding methods with these plants.

BACKGROUND OF THE INVENTION

Carrot (*Daucus carota* subsp. *sativus*), is a root vegetable, usually orange in color, though purple, red, white, and yellow varieties exist. It has a crisp texture when fresh. The most commonly eaten part of a carrot is a taproot, although the greens are edible as well. It is a domesticated form of the wild carrot *Daucus carota*, wildly believed to be from central Asia. Most of the modem breeding of the domestic carrot originated in Europe and which has focused on the selection of a greatly enlarged and more palatable, less woody-textured edible taproot. The annual purple varieties essentially missed out on those centuries of modem breeding until approximately the last 20 years. The world production of carrots and turnips for calendar year 2011 was almost 35.658 million tons (Food and Agriculture Organization of the United Nations (FAO)).

The aim of a vegetable breeder is to combine desirable traits in a single variety. Such desirable traits may include any trait deemed beneficial by a grower and/or consumer, including greater yield, resistance to insects or disease, tolerance to environmental stress, and nutritional value.

Total anthocyanin level is an example of such a desirable trait. Anthocyanins are polyphenols with known antioxidant activity which may be responsible for some biological activities including the prevention or lowering the risk of cardiovascular disease, diabetes, arthritis and cancer. Nevertheless, such properties, their stability and bioavailability depend on their chemical structure (Miguel M G. *Journal of Applied Pharmaceutical Science*. 01(06); 2011: 7-15.

A uniform population of a breeding line can be obtained by self-pollination and selection for type. Plants thus obtained become homozygous at almost all gene loci, i.e. a homozygous plant. Crossing two such plants of different genotypes produces a uniform population of plants that are heterozygous for many loci. On the other hand, a cross of two plants each heterozygous at a number of loci produces a population of plants that differ genetically and are not uniform. Due to this non-uniformity, performance of such plants is unpredictable.

Thus, a vegetable breeder prefers development of a homozygous inbred plant that can be crossed to produce uniform varieties. Pedigree breeding and recurrent selection are examples of breeding methods that have been used to develop inbred plants from breeding populations. Those breeding methods combine the genetic backgrounds from two or more plants or various other broad-based sources into breeding pools from which new lines derived therefrom are developed by selfing and selection of desired phenotypes. The new lines are evaluated to determine which of those have commercial potential.

So far, breeding efforts have provided a number of useful carrot lines with beneficial traits, however, there remains a great need in the art for new lines with further improved traits. There is thus a need for new carrot varieties having specific combination of trait or color.

SUMMARY OF THE INVENTION

The objective of the invention was to develop an Imperator type variety with purple coloration throughout and a high anthocyanin content of the mature root.

In one aspect, the present invention provides seed of a new carrot (*Daucus carota*) variety, designated Purple Royale, having been deposited under Accession Number PTA-127279, a plant, or a part thereof, produced by growing said seed. The invention also provides methods and compositions relating to plants, plant parts, seeds and progenies of carrot variety Purple Royale.

Variety Purple Royale is most similar to comparison variety Anthonina or Deep Purple, which is a variety produced and sold by Bejo. However, Purple Royale differs from Anthonina, Purple Elite, Purple Haze, and Deep Purple in one or more, e.g., at least two, at least three, optionally all morphological and/or physiological characteristics listed in the following (see also Table 1), when grown under the same environmental conditions:

an (average) root core thickness (at midpoint of cross-section) that is at least about 12%, or preferably at least about 13%, 14%, 15%, 16%, 17%, 18%, or even about 19% bigger than the core thickness of one or more of black carrot varieties Anthonina, Purple Elite, Purple Haze, and Deep Purple;

a (average) root diameter at midpoint that is at least about 7.5%, or preferably at least about 10%, 11%, 12%, 13%, 14%, or even about 14.9% smaller than the diameter at midpoint of one or more of black carrot varieties Anthonina, Purple Elite, Purple Haze, and Deep Purple;

a (average) carrot root length (minus taproot) that is at least about 5%, or preferably at least about 5.5%, 6%, 6.5%, 7%, 7.5%, 8%, or even about 8.3% smaller than the carrot length of one or more of black carrot varieties Anthonina, Purple Elite, Purple Haze, and Deep Purple;

a purple cross-section interior color of both core and cortex, which is darker than the purple cross-section interior color of Anthonina, Purple Elite, Purple Haze, and Deep Purple, e.g. N79A for Purple Royale versus the designation listed for the other carrot varieties in Table 1;

Other differences between variety Purple Royale and Anthonina, Purple Elite, Purple Haze, and Deep Purple reveals that Purple Royale also differs significantly from Anthonina, Purple Elite, Purple Haze, and Deep Purple in one or more, e.g., at least two, at least three, optionally all morphological and/or physiological characteristics listed in the following (see also Table 1), when grown under the same environmental conditions.

The present invention provides a carrot plant variety designated, representative seed of said variety having been deposited under ATCC Accession Number PTA-127279, and plant parts of the new variety such as for example seed, leaf, pollen, an ovule, taproot, root and a cell of the plant.

The invention also concerns the seed of the carrot Purple Royale, representative seed of said variety having been deposited under ATCC Accession Number PTA-127279, a plant, or a part thereof, produced by growing said seed. Or carrot plants having all or essentially all the physiological and morphological characteristics of Purple Royale.

The invention further relates to breeding methods using plants or seed of carrot variety Purple Royale.

Additional objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
FIG. 1 shows the presence of anthocyanin in Purple Royale.
Figure 2:
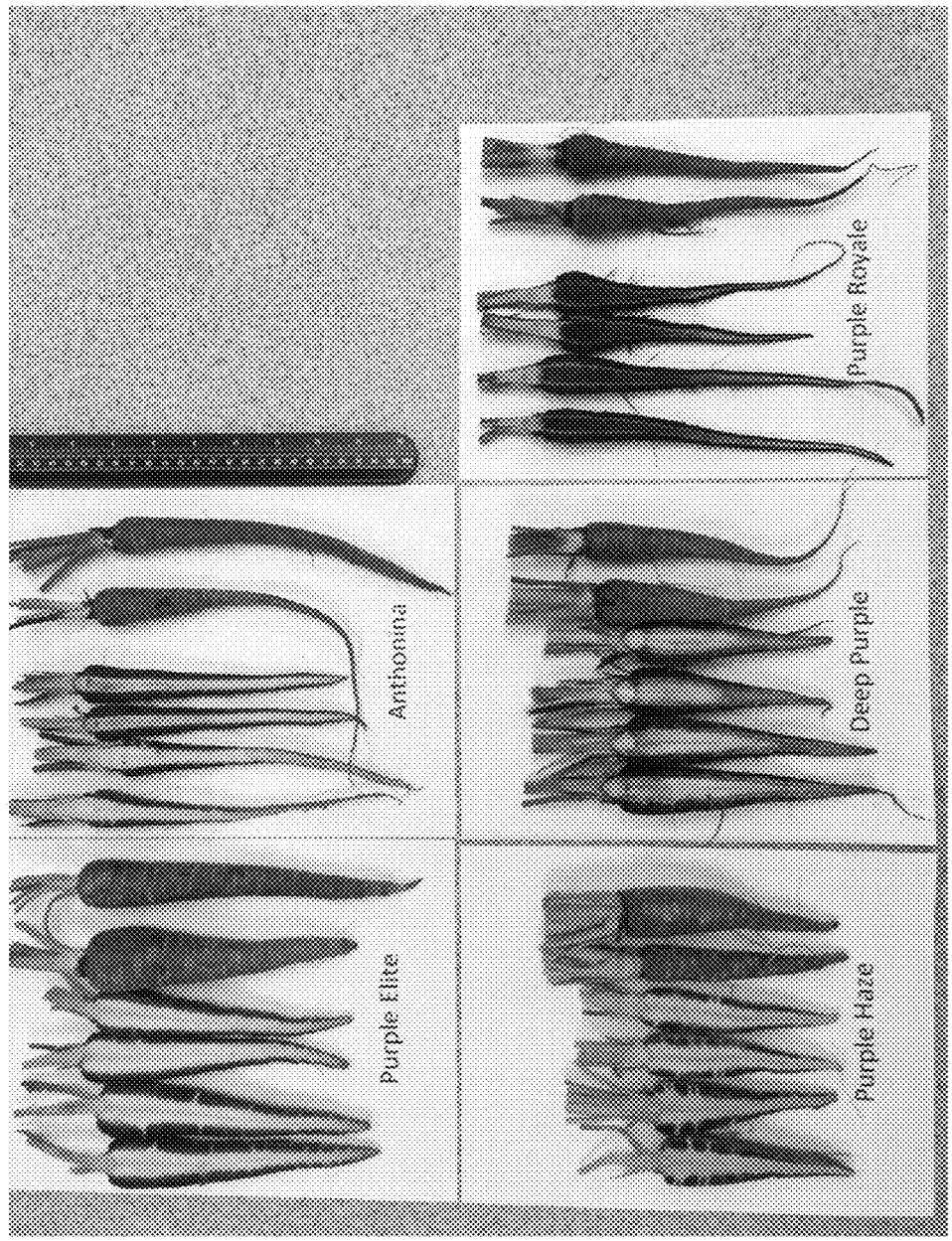
FIG. 2 shows the presence/absence of anthocyanin in Purple Royale, Anthonina, Purple Elite, Purple Haze, and Deep Purple.

The present invention provides a carrot plant, or part thereof, the roots of said plant. The invention further relates to plant parts of these plants such as for example seed, leaf, pollen, an ovule, taproot, root and a cell of the plant. In another aspect, the plant parts include leaf, pollen, an ovule, taproot, root and a cell of the plant. In yet another aspect, the plant part is a root.

The invention also includes seed of the plant of the plants of the invention, i.e seeds from which a carrot plant, the roots of which comprise, can be grown.

In another embodiment the invention concerns a plant according to the invention wherein the genetic elements conferring said total anthocyanin level is obtainable from carrot variety Purple Royale, a representative sample of seed of Purple Royale having been deposited under ATCC Accession Number PTA-127279.

In still another embodiment the invention relates to a plant according to the invention wherein the genetic elements conferring said are obtainable from carrot variety Purple Royale, a representative sample of seed of Purple Royale having been deposited under ATCC Accession Number PTA-127279.

Anthocyanin content is a function of growth stage and production environment.

In another aspect the root of the carrot plant of the invention has a total average anthocyanin level of at least about 20 ppm or preferably at least about 21 ppm, 22 ppm, 23 ppm, 24 ppm, 25 ppm, or even about 26 ppm. The anthocyanin content of the carrot variety Purple Royale will exceed any known carrot variety at all growth stages.

All parts of the specification which refer herein to variety Purple Royale, such as breeding, progeny, plant parts, cells, seeds, development of identification of EDVs, etc. can also be applied in a more general way, i.e. to methods for transfer the genetic elements conferring high anthocyanin levels. Thus, the invention not only relates to the above carrot plant, but also to cells, tissues, plant parts, seeds, EDVs, progeny, transformed carrot plants, etc. which comprise the genetic determinants obtainable from (obtained from; as present in) Purple Royale which confer the high anthocyanin content and optionally the genetic elements which confer the faint haloing and zoning.

The present invention provides a carrot plant variety designated Purple Royale, representative seed of said variety having been deposited under ATCC Accession Number PTA-127279, and plant parts of the new variety such as for example seed, leaf, pollen, an ovule, taproot, root and a cell of the plant. In another aspect, the plant parts include leaf, pollen, an ovule, taproot, root and a cell of the plant. In yet another aspect, the plant part is a root. Also provided are carrot plants having all or essentially all the physiological and morphological characteristics of such a plant, i.e. a carrot plant that does not differ (statistically) significantly from Purple Royale in the morphological and/or physiological characteristics of Table 1, when grown under the same conditions.

The invention also concerns the seed of the carrot Purple Royale, representative seed of said variety having been deposited under Accession Number ATCC PTA-127279, a plant, or a part thereof (e.g. a root), produced by growing said seed. Or carrot plants having all or essentially all the physiological and/or morphological characteristics of Purple Royale when grown under the same conditions. The carrot seed of the invention (i.e. seed from which a plant of variety Purple Royale can be grown) may be provided as an essentially homogeneous population of carrot seed according to the invention. Essentially homogeneous populations of seed are generally free from substantial numbers of other seed. Therefore, seed of the carrot Purple Royale or carrot plants having all or essentially all the physiological and/or morphological characteristics of Purple Royale may be defined as forming at least about 97% of the total seed, including at least about 98%, 99% or more of the seed. The seed population may be separately grown to provide an essentially homogeneous population of carrot plants according to the invention. Also provided are plants or plant parts such as seed (produced on the plant Purple Royale, e.g. after self-pollination or cross-pollination by another carrot plant), leaf, pollen, an ovule, taproot, roots or a cell produced by growing the seeds of the invention. In yet another aspect, the plant part is a root.

In another aspect the invention relates to a variety of Purple Royale having at least one, two or three physiological and/or morphological characteristics which are (statistically significantly) different from those of Purple Royale and which otherwise has essentially all physiological and morphological characteristics of a carrot plant designated Purple Royale, a representative sample of seeds of which having been deposited under ATCC Accession Number PTA-127279.

In another aspect, the invention relates to a variety of Purple Royale having at least one or two physiological and/or morphological characteristics which are significantly different from those of Purple Royale and which otherwise comprises at least 3, 4 or 5 or more (or all) of the distinguishing characteristics 1)-5) as defined below, or preferably at least 3, 4, 5, 6, 7, 8, 9, 10, 11, or 12 or all 12 of the distinguishing characteristics 1)-12) of Purple Royale and/or has essentially all physiological and morphological characteristics of a carrot plant designated Purple Royale obtainable by selecting a natural or induced mutant, or a somaclonal variant, or a natural variant from a population of plants designated Purple Royale.

In still another aspect, a carrot plant, or a part thereof, is provided which does not significantly differ in distinguishing characteristics 1)-5) of carrot plant Purple Royale when grown under the same conditions. In yet another aspect, the invention relates to a carrot plant, or a part thereof, which does not significantly differ in distinguishing characteristics 1)-5) and additionally comprises (i.e. does not differ statistically significantly in) at least one, two, three or all of distinguishing characteristics 6)-12) of carrot plant Purple Royale when grown under the same conditions.

In yet another aspect, the invention relates to a carrot plant, or a part thereof, which does not differ significantly from carrot plant Purple Royale in any of the physiological and/or morphological characteristics of Table 1 when grown under the same conditions.

In another aspect the invention relates to a carrot plant, or a part thereof, which does not significantly differ from carrot plant Purple Royale in any of the distinguishing characteristics (see USDA descriptors) consisting of 1) average root core thickness at midpoint of cross-section; 2) average root diameter at midpoint; 3) average carrot length (minus taproot); 4) cross-section interior color of both core and cortex; 5) haloing and zoning of the root at market maturity, when grown under the same conditions.

In still another aspect, a carrot plant is provided, which statistically significantly differs from Purple Royale in at least one morphological and/or physiological characteristic, but which does not differ significantly from Purple Royale in the following characteristics (see USDA descriptor) when grown under the same conditions: 1) average root core thickness at midpoint of cross-section; 2) average root diameter at midpoint; 3) average carrot length (minus taproot); 4) cross-section interior color of both core and cortex; 5) haloing and zoning of the root at market maturity.)

In a further aspect, a carrot plant is provided, which statistically significantly differs from Purple Royale in at least one morphological and/or physiological characteristics, but which does not differ significantly from Purple Royale in the following characteristics (see USDA descriptors) when grown under the same conditions: 1) average root core thickness at midpoint of cross-section; 2) average root diameter at midpoint; 3) average carrot length (minus taproot); 4) cross-section interior color of both core and cortex; 5) haloing and zoning of the root at market maturity; and which further does not significantly differ from the plant designated Purple Royale in one, two, three or more of the following characteristics when grown under the same conditions: 6) Petiole length from crown to first pinna; 7) average length of taproot; 8) leaf blade color (at harvest stage); 9) leaf blade divisions (at harvest stage); 10) leaf petiole anthocyanin level at harvest stage and petiole pubescence at harvest stage; 11) average root diameter at shoulder; 12) total anthocyanin level.

In a further embodiment a carrot plant is provided, which (statistically significantly) differs from the carrot plant designated Purple Royale, representative seeds of said carrot plant having been deposited under ATCC accession number, in at least one, two, three, four, or five morphological and/or physiological characteristics when grown under the same environmental conditions, whereby the morphological and/or physiological characteristics are those of Table 1. The carrot plant does, thus, not differ in a statistically significant way from Purple Royale in any of the morphological and/or physiological characteristics of Table 1 when grown under the same conditions, or only differs is one, two, three, four or five of the morphological and/or physiological characteristics of Table 1, while there is no significant difference in the other characteristics.

In one embodiment a carrot plant is provided, designated Purple Royale, which does not (statistically significantly) differ in any of the morphological and/or physiological characteristics of Table 1 from plants grown from seeds deposited under ATCC accession number PTA-127279 when grown under the same environmental conditions.

In yet another aspect of the invention, a tissue culture or cell-culture of regenerable cells of a carrot plant according to the invention is provided. The tissue culture or cell-culture will preferably be capable of regenerating carrot plants capable of expressing all of the physiological and/or morphological characteristics of the starting plant, and of regenerating plants having substantially the same genotype as the starting plant. Examples of some of the physiological and/or morphological characteristics of the carrot Purple Royale include those traits set forth in Table 1 herein when grown under the environmental conditions outlined herein with reference to the data of Table 1. The regenerable cells in such tissue or cell cultures may be derived, for example, from carrot explants, such as embryos, meristems, petioles, cuttings, protoplasts, cotyledons, pollen, leaves, nodes, anthers, roots, taproots, root tips, pistils, flowers, seed and stems. Still further, the present invention provides carrot plants regenerated from a tissue culture or cell culture of the invention. These plants have all the physiological and/or morphological characteristics of a plant according to the invention.

In another aspect, the above described carrot plants are obtainable from in vitro cell or tissue cultures. As already elsewhere in this application, in vitro cell or tissue cultures are known in the art and can be used to either vegetatively reproduce the plant from which the cells or tissues were obtained or to identify and/or select a phenotypic variant (such as an EDV), and to regenerate such a variant. The phenotypic variant may, for example, be a somaclonal variant, mutant or off-type, but is preferably genetically stable. Thus, the variant phenotype is preferably genetically stable, also in the mature plants regenerated from the cell or tissue culture. That means, the phenotypic variant does not show variation in phenotype which are transient and are not genetically stable. Once selected, such selected variants can then in turn also be reproduced true to type using in vitro cell or tissue culture or by propagation via seed.

Thus, in one aspect, a carrot plant is provided which is clonally propagated (it is a vegetative reproduction) from Purple Royale cells or tissue and which comprises all the distinguishing characteristics of Purple Royale when grown under the same environmental conditions. In another aspect it further comprises one or more of the further distinguishing characteristics. In yet another aspect it comprises all morphological and/or physiological characteristics of Purple Royale as given in Table 1. And in yet a further aspect it comprises all morphological and/or physiological characteristics of Purple Royale as given in Table 1, except that it significantly differs from Purple Royale in one, two, three, four, or five of the morphological and/or physiological characteristics of Table 1.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets.

In still yet another aspect of the invention, processes are provided for producing carrot seeds, plants and roots, which processes generally comprise crossing a first parent carrot plant with a second parent carrot plant, wherein at least one of the first or second parent carrot plants is a plant according to the invention.

One embodiment of the invention refers to a method of producing a carrot plant comprising crossing a carrot plant of variety Purple Royale with a second carrot plant one or more times such as one, two, three, four, five, six or more times. This method comprises in one embodiment selecting progeny from said crossing.

These processes may be further exemplified as processes for preparing the carrot seed or plants, wherein a first carrot plant is crossed with a second carrot plant of a different, distinct genotype to provide a plant that has, as one of its parents, a plant of Purple Royale.

The present invention also provides the carrot seeds and plants produced by a process that comprises crossing a first parent carrot plant with a second parent carrot plant, wherein at least one of the first or second parent carrot plants is a plant provided herein, such as from the variety Purple Royale. In another embodiment of the invention, carrot seed and plants produced by the process are first filial generation (F1) carrot seed and plants produced by crossing a plant in accordance with the invention with another, distinct plant. The present invention further contemplates plant parts of such an $F_1$ carrot plant, and methods of use thereof. Therefore, certain exemplary embodiments of the invention provide an $F_1$ carrot plant and seed thereof.

In another embodiment of the invention, carrot variety Purple Royale is crossed to produce seed of the variety designated Purple Royale. In any cross herein, either parent may be the male or female parent. In these processes, crossing will result in the production of seed. The seed production occurs regardless of whether the seed is collected or not.

In certain embodiments, the invention provides methods of introducing a desired trait into a carrot plant comprising the steps of: (a) crossing a plant of variety Purple Royale with a second carrot plant that comprises a desired trait to produce F 1 progeny, (b) selecting an F1 progeny that comprises the desired trait(s), e.g., one, two, three or more desired trait(s), (c) optionally selfing the F1 progeny one or more times to produce F2, F3, or further generation selfing progeny, crossing the selected F1 progeny or the selfing progeny with a plant of variety Purple Royale to produce backcross progeny, and (e) selecting backcross progeny comprising the desired trait(s) and which otherwise has all or essentially all the physiological and morphological characteristics of carrot variety Purple Royale, (f) optionally, steps (d) and (e) can be repeated one or more times, e.g., three or more times such as three, four, five, six or seven times, in succession to produce higher backcross progeny (e.g., selected fourth, fifth, sixth, seventh or eighth or higher backcross progeny) that comprises the desired trait. The invention also provides carrot plants produced by these methods; a representative sample of seed of Purple Royale having been deposited under ATCC Accession Number PTA-127279.

In another aspect of the invention, a carrot plant of variety Purple Royale comprising an added heritable trait (in addition to all the morphological and/or physiological characteristics of Purple Royale) or a modified heritable trait is provided, e.g., an Essentially Derived Variety of Purple Royale (such as a mutant, or off-type, natural variant or somaclonal variant) having one, two or three physiological and/or morphological characteristics which are different from those of Purple Royale and which otherwise has all the physiological and morphological characteristics of Purple Royale, wherein a representative sample of seed of variety Purple Royale has been deposited under ATCC Accession Number PTA-127279. The heritable trait may comprise a genetic locus that is, for example, a dominant or recessive allele. In one embodiment of the invention, a plant of the invention is defined as comprising a single locus conversion. For example, one, two, three or more heritable traits may be introgressed at any particular locus using a different allele that confers the new trait or traits of interest. In specific embodiments of the invention, the single locus conversion confers one or more traits such as, for example, herbicide tolerance, insect resistance, disease resistance and modulation of plant metabolism and metabolite profiles. In further embodiments, the trait may be conferred by a naturally occurring gene introduced into the genome of the variety by backcrossing, a natural or induced mutation, a somaclonal variant, an off-type, or a transgene introduced through genetic transformation techniques into the plant or a progenitor of any previous generation thereof. When introduced through transformation, a genetic locus may comprise one or more genes integrated at a single chromosomal location. Thus, the invention comprises a method of producing a plant comprising an added desired trait, the method comprising introducing a transgene conferring a desired trait into a plant of carrot variety Purple Royale.

In still yet another aspect, the invention provides a method of determining the genotype of a plant of the invention comprising detecting in the genome of the plant at least a first polymorphism. The method may, in certain embodiments, comprise detecting a plurality of polymorphisms in the genome of the plant. For example, a sample of nucleic acid is obtained from a plant and a polymorphism or a plurality of polymorphisms is detected in said nucleic acids. The method may further comprise storing the results of the step of detecting the plurality of polymorphisms on a computer readable medium.

In one embodiment of the invention, the invention provides a method for producing a seed of a variety derived from Purple Royale comprising the steps of (a) crossing a carrot plant of variety Purple Royale with a second carrot plant; and (b) allowing seed of a variety Purple Royale-derived carrot plant to form. This method can further comprise steps of (c) crossing a plant grown from said variety Purple Royale-derived carrot seed with itself or a second carrot plant to yield additional variety Purple Royale-derived carrot seed; (d) growing said additional variety Purple Royale-derived carrot seed of step (c) to yield additional variety Purple Royale-derived carrot plants; and optionally (e) repeating the crossing and growing steps of (c) and (d) to generate further variety Purple Royale-derived carrot plants, e.g. one or more times such as two times, three times, three or more times such as four times, five times, six times, seven times or even more times. For example, the second carrot plant is of an inbred carrot variety, or alternatively, the second carrot plant in step c) is Purple Royale or the male or female parent plant of Purple Royale.

In still yet another aspect, the present invention provides a method of producing a plant or a seed derived from variety Purple Royale, the method comprising the steps of: (a) preparing a progeny plant derived from said variety by crossing a plant of variety Purple Royale with a second plant; and (b) allowing seed of a variety Purple Royale-derived carrot plant to form. In one embodiment, the second plant is a plant of an inbred line or of a wild accession of *Daucus carota*.

The method may additionally comprise: (c) crossing a plant grown from said variety Purple Royale-derived carrot seed with itself or a second carrot plant to yield additional variety Purple Royale-derived carrot seed; (d) growing said additional variety Purple Royale-derived carrot seed of step (c) to yield additional variety Purple Royale-derived carrot plants; and optionally (e) repeating the crossing and growing steps of (c) and (d) to generate further variety Purple Royale-derived carrot plants. For example, steps (c) and (d) may be repeated one or more times such as one, two, three, four five or six, seven, eight, nine, ten, or more times to produce a further plant derived from the aforementioned starting variety. The further plant derived from variety Purple Royale may be an inbred variety, and the aforementioned repeated crossing steps may be defined as comprising sufficient inbreeding to produce the inbred variety. In the method, it may be desirable to select particular plants resulting from step (c) for continued crossing according to steps (b) and (c). By selecting plants having one or more desirable traits, a plant is obtained which possesses some of the desirable traits of the starting plant as well as potentially other selected traits.

In certain embodiments, the present invention provides a method of producing a carrot root comprising: (a) obtaining a plant of the invention, wherein the plant has been cultivated to maturity, and (b) collecting the carrot root from said plant.

The invention also provides for a food or feed product comprising or consisting of a plant part described herein preferably a carrot root or part thereof and/or an extract from a plant part described herein. The food or feed product may be fresh or processed, e.g., canned, steamed, boiled, fried, blanched and/or frozen, etc.

In still another embodiment the invention relates to a seed or plant produced by selfing a plant of the invention.

In another aspect the invention refers to packages, e.g., a container, a bag and the like, comprising at least one of the following: seeds or seed pellets of carrot variety designated Purple Royale, carrot plant(s) designated Purple Royale, parts thereof (e.g. roots), progeny of a carrot plant designated Purple Royale, parts thereof, EDV of a plant designated Purple Royale or parts thereof.

In one embodiment any of the plant of the invention comprises at least 3, 4, 5 or more of the (average) morphological and/or physiological characteristics as described in Table 1 for the carrot variety Purple Royale.

Another aspect refers to a carrot plant, or a part thereof, having all or essentially all the physiological and/or morphological characteristics of a carrot plant of carrot variety Purple Royale when grown under the same conditions.

Also provided are one or more progeny plants (offspring or descendants) of a carrot plant designated Purple Royale obtained by further breeding with said variety designated Purple Royale. Said progeny plant(s) has/have essentially all physiological and/or morphological characteristics of variety Purple Royale when grown under the same environmental conditions. In one embodiment, said progeny plant(s) has/have 3, 4, 5, 6, 7, 8, or more, or all of, the following (average) characteristics (see USDA descriptors) as described in Table 1.

Any embodiment discussed herein with respect to one aspect of the invention applies to other aspects of the invention as well, unless specifically noted.

In the description and tables herein, a number of terms are used. In order to provide a clear and consistent understanding of the specification and claims, the following definitions are provided:

The term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and to "and/or."

When used in conjunction with the word "comprising" or other open language in the claims, the words "a" and "an" denote "one or more" unless specifically noted.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. The terms mentioned above also comprise the term "contain" which is limited to specific embodiments. Thus, one embodiment of the invention, when the terms "comprise," "have" and "include" are used to describe a plant, part thereof or a process, refers to an embodiment wherein the limiting term "contain" is used.

"Carrot" refers herein to a plant of the species *Daucus carota* and parts thereof, e.g., the (edible) root. The most commonly eaten part of a carrot is a root, although the greens are edible as well. A carrot is a root vegetable plant, the root (carrot root) is usually orange in color, though purple, red, white, and yellow varieties exist, as well. At the tip of a carrot root is a thin taproot while at the other end (base) of a carrot root the green is attached.

"Cultivated carrot" refers to plants of *Daucus carota*, i.e. varieties, breeding lines or cultivars of the species *Daucus carota*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"USDA descriptors" are the plant variety descriptors described for carrot in the "Objective description of Variety Carrot *Daucus carota*)", ST-470-78 (as published by U.S. Department of Agriculture, Agricultural Marketing Service, Science and Technology, Plant Variety Protection Office, Beltsville, Md. 20705.

"UPOV descriptors" are the plant variety descriptors described for carrot in the "Guidelines for the Conduct of Tests for Distinctness, Uniformity and Stability, TG/49/8 (Geneva 2007), as published by UPOV (International Union for the Protection of New Varieties and Plants) and is herein incorporated by reference in its entirety.

"Core" refers to the phloem and xylem of the root, i.e. the central vascular tissue.

"Cortex" refers to the non-vascular tissue surrounding the core tissue.

"Genotype" refers to the genetic composition of a cell or organism.

"Phenotype" refers to the detectable characteristics of a cell or organism, which characteristics are the manifestation of gene expression.

As used herein, the term "plant" includes the whole plant or any parts or derivatives thereof, preferably having the same genetic makeup as the plant from which it is obtained, such as plant organs (e.g. harvested or non-harvested carrot root), plant cells, plant protoplasts, plant cell and/or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, flowers, leaves, seeds, clonally propagated plants, roots, taproots, stems, root tips, grafts, parts of any of these and the like. Also, any developmental stage is included, such as seedlings, cuttings prior or after rooting, mature plants, roots or leaves. Alternatively, plant part may also include a plant seed which comprises one or two sets of chromosomes derived from the parent plant.

"Harvested plant material" refers herein to plant parts (e.g. a root detached from the whole plant) which have been collected for further storage and/or further use.

"Harvested seeds" refers to seeds harvested from a line or variety, e.g. produced after self-fertilization or cross-fertilization and collected.

A plant having "(essentially) all the physiological and/or morphological characteristics" means a plant having essentially all or all the physiological and/or morphological characteristics when grown under the same environmental conditions of the plant of Purple Royale from which it was derived, e.g. the progenitor plant, the parent, the recurrent parent, the plant used for tissue- or cell culture, etc. The skilled person will understand that a comparison between carrot varieties should occur when said varieties are grown under the same environmental conditions. For example, the plant may have all characteristics mentioned in Table 1 when grown under the environmental conditions outlined herein with reference to the data of Table 1. In certain embodiments, the plant having "essentially all the physiological and/or morphological characteristics" are plants having all the physiological and/or morphological characteristics of Table 1, except for certain characteristics, such as one, two or three, mentioned, e.g. the characteristic(s) derived from a converted or introduced gene or trait and/or except for the characteristics which differ in an EDV. So, the plant may have all characteristics mentioned in Table 1, except for one, two or three characteristics of Table 1, in which the plant may thus differ.

A plant having one or more or all "essential physiological and/or morphological characteristics" or one or more "distinguishing characteristics" (such as one, two, three, four or five) refers to a plant having (or retaining) one or more, or all, or retaining all except one, two or three of the distinguishing characteristics mentioned in Table 1 when grown under the same environmental conditions that distinguish Purple Royale from most similar varieties Anthonina, Purple Elite, Purple Haze, and Deep Purple. For example, such distinguishing characteristics being selected from (but not limited to): 1) average root core thickness at midpoint cross-section, 2) average root diameter at midpoint, 3) carrot length (minus taproot), 4) cross-section interior color of core and cortex, 5) haloing and zoning of the root at market maturity, 6) Petiole length from crown to first pinna, 7) average length of taproot, 8) blade color of leaf at harvest stage, 9) blade divisions of leaf at harvest stage, 10) leaf petiole anthocyanin level and petiole pubescence at harvest stage, 11) average rood diameter at shoulder (see USDA descriptors, and 12) total anthocyanin levels.

The physiological and/or morphological characteristics mentioned above are commonly evaluated at significance levels of 1%, 5%, 8% or 10% significance level, when measured under the same environmental conditions. For example, a progeny plant of Purple Royale may have one or more (or all, or all except one, two or three) of the essential physiological and/or morphological characteristics of Purple Royale listed in Table 1, or one or more or all (or all except one, two or three) of the distinguishing characteristics of Purple Royale listed in Table 1 and above, as determined at the 1% or 5% significance level when grown under the same environmental conditions.

Physiological and/or morphological characteristics which are "substantially equivalent" or "not significantly different" or "not significantly differ" refers to a characteristic that, when compared, does not show a statistically significant difference (e.g., $p \geq 0.05$ using ANOVA) from the mean. Vice versa, "significantly different" or "statistically significantly different" refers to a characteristic that, when compared, does show a statistically significant difference (e.g., $p < 0.05$ using ANOVA) from the mean.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

The terms "gene converted" or "conversion plant" in this context refer to carrot plants which are often developed by backcrossing wherein essentially all of the desired morphological and/or physiological characteristics of parent are recovered in addition to the one or more genes transferred into the parent via the backcrossing technique or via genetic engineering. Likewise, a "Single Locus Converted (Conversion) Plant" refers to plants which are often developed by plant breeding techniques comprising or consisting of backcrossing, wherein essentially all of the desired morphological and physiological characteristics of a carrot variety are recovered in addition to the characteristics of the single locus having been transferred into the variety via, e.g., the backcrossing technique and/or by genetic transformation. Likewise, a double-loci converted plant/a triple loci converted plant refers to plants having essentially all of the desired morphological and/or physiological characteristics of given variety, expect that at two or three loci, respectively, it contains the genetic material (e.g., an allele) from a different variety.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, or an off-type, or the selection of a (natural) variant individual from plants of the initial variety, backcrossing, or transformation by genetic engineering. Such a variant may be selected at any time, e.g. in the field or greenhouse, during breeding, during or after in vitro culture of cells or tissues, during regeneration of plants, etc. The term EDV, thus, also encompassed a "phenotypic variant" derived from Purple Royale seed, plant tissue or cells. In one embodiment, an EDV is a gene converted plant.

"Plant line" is for example a breeding line which can be used to develop one or more varieties.

"Progeny" (or "descendants") as used herein refers to plants derived from a plant designated Purple Royale. Progeny may be derived by regeneration of cell culture or tissue culture or parts of a plant designated Purple Royale or selfing of a plant designated Purple Royale or by producing seeds of a plant designated Purple Royale. In further embodiments, progeny may also encompass plants derived from crossing of at least one plant designated Purple Royale with another carrot plant of the same or another variety or (breeding) line, or with a wild carrot plant, backcrossing, inserting of a locus into a plant or selecting a plant comprising a mutation or selecting a variant. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Especially progeny of Purple Royale which are EDVs or which retain all (or all except 1, 2 or 3) physiological and/or morphological characteristics of Purple Royale listed in Table 1, or which retain all (or all except 1, 2, or 3) of the distinguishing characteristics of Purple Royale described elsewhere herein and in Table 1, are encompassed herein.

The term "traditional breeding techniques" encompasses herein crossmg, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one carrot line or variety to another.

"Crossing" refers to the mating of two parent plants.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Selfing" refers to self-pollination of a plant, i.e., the transfer of pollen from the anther to the stigma of the same plant.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, nodes, protoplasts, meristematic cell, root, root tip, pistil, anther, flower, shoot tip, shoot, stem, petiole, etc. When a whole plant is regenerated by vegetative propagation, it is also referred to as a vegetative propagation.

The term "locus" (loci plural) means a specific place or places or a site on a chromosome where for example a gene or genetic marker is found. "Linkage" or "genetic linkage" is the tendency of genes genes or molecular markers that are located proximal to each other on a chromosome chromosome to be inherited together during meiosis. Genes or molecular markers whose loci are nearer to each other are less likely to be separated onto different chromatids chromatids during chromosomal crossover chromosomal crossover and are therefore said to be genetically linked.

"Marker" or "molecular marker" refers to a readily detectable DNA sequence or nucleotide, which may be genetically closely linked to a gene or locus. Such closely linked markers can be used in MAS (marker assisted selection) of the gene or locus.

"Marker assisted selection" or "MAS" is a process of using the presence of molecular markers, which are genetically linked to a particular locus or to a particular chromosome region, to select plants for the presence of the specific locus or region.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

As used herein, the terms "resistance" and "tolerance" are used interchangeably to describe plants that show no symptoms or significantly reduced symptoms to a specified biotic pest, pathogen, abiotic influence or environmental condition. These terms are also used to describe plants showing some symptoms but that are still able to produce marketable product with an acceptable yield.

"Tissue Culture" refers to a composition comprising isolated cells or tissues of the same or a different type or a collection of such cells organized into parts of a plant.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for carrot described herein. The mean, if not indicated otherwise within this application, refers to the arithmetic mean of measurements on at least 10 different, randomly selected plants or plant parts of a variety or line.

As used herein, the term "anthocyanin" refers to anthocyanins with sugar group(s), mostly 3-glucosides of the cyanidins, though other 3-glycosides and 5-glycosides are also known (Stintzing et al. Agric Food Chem. 2002. Vol 50. 6172-6181). The anthocyanins can be subdivided into the sugar-free anthocyanidin aglycone and the anthocyanin glycosides. The difference in chemical structure that occurs in response to changes in pH is the reason why anthocyanins are often used as pH indicators, as they change from red in acids to blue in bases (i.e. basic environment such as pH>7 or >8 or even pH>9 or >10 or >11).

The term "total anthocyanin level" or "total anthocyanin content" refers to the amount of anthocyanins in the root of the carrot at market maturity. Whenever reference is made to "total anthocyanin level", the combined level of all glycosides of anthocyanidin together is being referred to, without identifying individual anthocyanins. Different parts of the root of a carrot may contain different levels of anthocyanin e.g. sampling root shoulder vs root tips will give different results. The middle section (between top and shoulder) of a carrot gives a good sample of the anthocyanin level of the major part of a carrot. Total anthocyanin levels may also depend somewhat depending on the trial location and sampling moment (e.g. stage of growth), however when measured under the same conditions, the variation between genotypes remains relatively stable and the ranking of genotypes does not change.

The total anthocyanin level per carrot can be determined using methods known in the art for example by purifying fresh carrot (whole carrot root, excluding tap root), optionally add an internal standard like malvidin-3-galactoside chloride to determine extraction efficacy, extract with 10% formic acid in methanol five times, centrifuge the extracts and combine the supernatants. Anthocyanins can then be determined by HPLC e.g. by using a C18 column and a mobile phase A of 10% formic acid in water and a mobile phase B of methanol using a gradient of B from 0 to 55%. Anthocyanins can be identified by comparing retention times and UV or MS spectra with known anthocyanins. A standard response curve for quantifying the anthocyanin may be prepared from cyanidin-3-glucoside.

The term "genetic elements conferring the total anthocyanin level" refers to all genes responsible for the total anthocyanin level in the root of a carrot plant.

The term "genetic elements conferring the level of haloing and zoning" refers to all genes responsible for the level of haloing and zoning in the root of a carrot plant.

Genetic elements conferring a specific trait may for example be determined using methods known in the art such as whole exome sequencing (also known as targeted exome capture) which is an approach that involves using sequencing technology and sequence assembly tools to piece together all coding portions of the genome. The sequence is then compared to a reference genome and any differences are noted. After filtering out all known polymorphisms, synonymous changes, and intronic changes (that do not affect splice sites), only potentially trait affecting variants will be left. This technique can be combined with other techniques to further exclude potentially trait-affecting variants should more than one be identified. Alternatively, genetic approaches, such as gene mapping or Quantitative Trait Analysis (using e.g. Bulk Segregant Analysis, as described by Michelmore et al. *Proc Natl Acad Sci USA*. 1991 Nov. 1; 88(21): 9828-9832 may be used to identify the number and location of genes which determine the trait and molecular markers linked to the genes or genome regions which determine the trait.

Seeds of the Carrot Variety Purple Royale.

Also provided are seeds of carrot variety Purple Royale, i.e. seeds from which the variety can be grown.

In one embodiment, a plurality of Purple Royale seeds are packaged into small and/or large containers (e.g., bags, cartons, cans, etc.). Seeds may be treated with one or more chemical compounds and/or biological control agents (e.g. to improved germination, insecticidal-, acaricidal-, nematicidal- or fungicidal-compounds or compositions, etc.) and/or seeds may be primed. Biological control agents are one or more microorganisms which protect the seed or seedling against pathogens. For example, strains of bacteria and/or fungi, such as bacteria of the species of *Streptomyces, Pseudomonas, Bacillus* and *Enterobacter* or fungi of the species *Phomopsis, Ectomycorrhizae, Trichoderma, Cladosporium* and *Gliocladium*.

Priming is a water-based process that is performed on seeds to increase uniformity of germination and emergence from the soil, and thus enhance vegetable stand establishment. Methods how to prime carrot seeds are well known in the art, see WO2008/107097, describing different priming methods, such as hydro-priming (including drum-priming), osmo-priming and solid-matrix priming, which can be used. The priming process may also be combined with the chemical compounds or compositions and/or biological control agent treatment, so seeds may e.g. be hydrated in a first step, dried in a second step and treated in a third step with one or more seed treatment compounds or compositions. Priming is also sometimes referred to as seed conditioning.

Hydropriming includes those techniques in which seeds are allowed to take up water for a short period or at low temperatures, mostly at ample water supply. These techniques are sometimes also referred to as soaking or steeping. With osmo-priming, the seeds are exposed to an osmotic solution (see e.g. WO2008/107097).

With solid matrix priming (SMP), seeds are mixed with water and solid carriers. Examples of solid carriers are vermiculite and diatomaceous silica products. The water is taken up by the seeds as well as absorbed on the solid particle surfaces, which in this way control the water uptake of the seeds. In addition to using particle-like carriers, SMP can be carried out using, amongst others, moist towels, gunny bags, moist sand, sterilized compost or press mud as well.

So, in one aspect seeds of Purple Royale are provided wherein said seeds are primed seeds and/or chemically and/or biologically treated seeds, comprising one or more chemical compounds or compositions and/or one or more biological control agents, selected from the group consisting of: a compound that improves germination, an insecticidal compound, an acaricidal compound, a nematicidal compound, and a fungicidal compound.

Breeding with Carrot Plants of the Invention

One aspect of the current invention concerns methods for crossing a carrot variety provided herein with itself or a second carrot plant and the seeds and plants produced by such methods. These methods can be used for propagation of a variety provided herein or can be used to produce carrot seeds and the plants grown therefrom. Such seed can be produced by crossing two parent lines or varieties to produce the variety.

In one embodiment of the invention, the first step in "crossing" comprises planting seeds of a first and a second parent carrot plant, often in proximity so that pollination will occur for example, mediated by insect vectors. Alternatively, pollen can be transferred manually. Where the plant is self-pollinated, pollination may occur without the need for direct human intervention other than plant cultivation.

Also in accordance with the invention, novel varieties may be created by crossing a plant of the invention followed by multiple generations of breeding according to such well known methods. New varieties may be created by crossing with any second plant. In selecting such a second plant to cross for the purpose of developing novel varieties, it may be desired to choose those plants that either themselves exhibit one or more selected desirable characteristics or that exhibit the desired characteristic(s). Once initial crosses have been made, inbreeding and selection take place to produce new varieties. For development of a uniform variety, often five or more generations of selfing and selection are involved.

Uniform varieties of new varieties may also be developed by way of double-haploids. This technique allows the creation of true breeding varieties without the need for multiple generations of selfing and selection. In this manner, true breeding varieties can be produced in as little as one generation. Haploid cells, such as microspores, pollen, anther cultures, or ovary cultures can be used. The chromosomes of the haploid cells may then be doubled autonomously, or by chemical treatments (e.g. colchicine treatment). From the double-haploid cells, fertile homozygous plants are obtained. In accordance with the invention, any of such techniques may be used in connection with a plant of the invention and progeny thereof to achieve a homozygous variety.

Backcrossing can also be used to improve an inbred plant. Backcrossing transfers one or more heritable traits from one inbred or non-inbred source to an inbred that lacks those traits. The exact backcrossing protocol will depend on the characteristic(s) or trait(s) being altered to determine an appropriate testing protocol. When the term variety Purple Royale is used in the context of the present invention, this also includes plants modified to include at least a first desired heritable trait such as one, two or three desired heritable trait(s).

This can be accomplished, for example, by first crossing a superior inbred (recurrent parent) to a donor inbred (non-recurrent parent), which carries the appropriate genetic information (e.g., an allele) at the locus or loci relevant to the trait in question. The progeny of this cross is then mated back to the recurrent parent followed by selection in the resultant progeny (first backcross generation, or BC1) for the desired trait to be transferred from the non-recurrent parent. After five or more backcross generations with selection for the desired trait, the progeny is heterozygous at loci controlling the characteristic being transferred but are like the superior parent for most or almost all other loci. The last backcross generation would be selfed to give pure breeding progeny for the trait being transferred.

The parental carrot plant which contributes the desired characteristic or characteristics is termed the non-recurrent parent because it can be used one time in the backcross protocol and therefore need not recur. The parental carrot plant to which the locus or loci from the non-recurrent parent are transferred is known as the recurrent parent as it is used for several rounds in the backcrossing protocol.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection or screening may be applied where the single locus (e.g. allele) acts in a dominant fashion. For example, when selecting for a dominant allele providing resistance to a bacterial disease, the progeny of the initial cross can be inoculated with bacteria prior to the backcrossing. The inoculation then eliminates those plants which do not have the resistance, and only those plants which have the resistance allele are used in the subsequent backcross. This process is then repeated for all additional backcross generations.

Although backcrossing methods are simplified when the characteristic being transferred is a dominant allele, recessive, co-dominant and quantitative alleles may also be transferred. In this instance, it may be necessary to introduce a test of the progeny to determine if the desired locus has been successfully transferred. In the case where the non-recurrent variety was not homozygous, the F1 progeny would not be equivalent. F1 plants having the desired genotype at the locus of interest could be phenotypically selected if the corresponding trait was phenotypically detectable in a heterozygous or hemizygous state. In the case where a recessive allele is to be transferred and the corresponding trait is not phenotypically detectable in the heterozygous of hemizygous state, the resultant progeny can be selfed, or crossed back to the donor to create a segregating population for selection purposes. Non-phenotypic tests may also be employed. Selected progeny from the segregating population can then be crossed to the recurrent parent to make the first backcross generation (BC1).

Molecular markers may also be used to aid in the identification of the plants containing both a desired trait and having recovered a high percentage of the recurrent parent's genetic complement. Selection of carrot plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross and can be used in selection of progeny for continued breeding. This technique is commonly referred to as marker assisted selection. Any other type of genetic marker or other assay that is able to identify the relative presence or absence of a trait of interest in a plant can also be useful for breeding purposes. Procedures for marker assisted selection applicable to the breeding of carrot are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs), Simple Sequence Repeats (SSR), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs).

Carrot varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

The variety of the present invention are particularly well suited for the development of new varieties based on the elite nature of the genetic background of the variety. In selecting a second plant to cross with Purple Royale for the purpose of developing novel carrot varieties, it will typically be preferred to choose those plants that either themselves exhibit one or more selected desirable characteristics or that exhibit the desired characteristic(s). Examples of desirable characteristics may include, but are not limited to herbicide tolerance, pathogen resistance (e.g., insect resistance, nematode resistance, resistance to bacterial, fungal, and viral disease), cytoplasmic male sterility (CMS), improved harvest characteristics, enhanced nutritional quality, increased antioxidant content, improved processing characteristics, high yield, improved characteristics related to the carrot root flavor, texture, size, shape, durability, shelf life, and yield, increased soluble solids content, uniform ripening, delayed or early ripening, seedling vigor, adaptability for soil conditions, and adaptability for climate conditions.

Deposit Information: In accordance with 37 C.F.R. §§ 1.801-1.809, a representative sample of seeds of Carrot Variety Purple Royale has been deposited and accepted, under the terms of the Budapest Treaty, with the American Type Culture Collection (ATCC), 10801 University Boulevard, Manassas, Va. 20110-2209 on Mar. 15, 2022, and has been assigned Accession No. PTA-127279. All restrictions upon availability to the public will be irrevocably removed upon granting of the patent.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXAMPLES

Example 1

Development of Carrot Variety Purple Royale

The variety Purple Royale can be developed from two replications of 50 plants each, from which 15 plants or plant parts can be randomly selected and used to measure characteristics. Table 1 provides the USDA descriptors for Purple Royale (this patent application), and of Anthonina, Purple Elite, Purple Haze, and Deep Purple (commercial reference varieties).

In accordance with one aspect of the present invention, provided is a plant having essentially all physiological and/or morphological characteristics of a carrot variety Purple Royale. A description of the physiological and/or morphological characteristics of carrot variety Purple Royale is presented in Table 1.

A. Characteristics of Purple Royale

TABLE 1

The USDA descriptors for Purple Royale, Anthonina, Purple Elite, Purple Haze, and Deep Purple a field trial. The values are mean values.

| USDA Descriptor | Purple Royale | Anthonina | Purple Elite | Purple Haze | Deep Purple |
|---|---|---|---|---|---|
| 1. TYPE:<br>1 = Amsterdam; 2 = Flakee; 3 = Berlicum; 4 = Chantenay; 5 = Danvers; 6 = Imperator; 7 = Nantes; 8 = Other (Specify) | 6 | 6 | 6 | 6 | 6 |
| 2. REGION OF ADAPTATION IN THE UNITED STATES OF AMERICA:<br>1 = Northeast; 2 = Northwest; 3 = Southeast; 4 = Southwest; 5 = North Central; 6 = South Central; 7 = Most Regions | 7 | 7 | 7 | 7 | 7 |
| 3. MARKET MATURITY:<br>No. Days from Seeding to Harvest | NA | NA | NA | NA | NA |
| 4. PLANT TOP: {At Harvest Stage} | NA | NA | NA | NA | NA |
| Habit:<br>1 = Erect; 2 = Semi-erect; 3 = Prostrate | 2 | 2 | 2 | 2 | 2 |
| Plant Top Height (from Shoulder to Top of Crown) | 33.44 cm | 40.69 cm | 39.39 cm | 39.46 cm | 40.15 cm |
| Plant Top Neck Diameter | 1.23 cm | 1.62 cm | 1.41 cm | 1.55 cm | 1.41 cm |
| Top Attachment:<br>1 = Single; 2 = Multiple | 1 | 1 | 1 | 1 | 1 |
| 5. LEAF: {At Harvest Stage}<br>Name of Color Chart: RHS | | | | | |
| Blade Color: 1 = Light Green; 2 = Medium Green; 3 = Dark Green; 4 = Other (Specify) | 1 | 2 | 2 | 2 | 2 |
| Color Chart Value | Blue Green | Green | Green | Green | Green |
| Color Chart Value Number | 120C | N134B | N134B | 139B | 135B |
| Blade Divisions:<br>1 = Fine; 2 = Medium; 3 = Coarse | 2 | 2 | 2 | 2 | 2 |
| Blade Length (Without Petiole) | 20.54 cm | 22.88 cm | 23.53 cm | 20.73 cm | 20.20 cm |
| Petiole Length from Crown to First Pinna | 14.64 cm | 22.75 cm | 22.48 cm | 21.69 cm | 24.25 cm |
| | 5.50 cm | 7.71 cm | 7.74 cm | 7.73 cm | 6.80 cm |
| Petiole Anthocyanin:<br>1 = Absent; 2 = Present | 2 | 2 | 2 | 2 | 2 |

TABLE 1-continued

The USDA descriptors for Purple Royale, Anthonina, Purple Elite, Purple Haze, and Deep Purple a field trial. The values are mean values.

| USDA Descriptor | Purple Royale | Anthonina | Purple Elite | Purple Haze | Deep Purple |
|---|---|---|---|---|---|
| Petiole Pubescence<br>1 = Absent; 2 = Present | 2<br>(heavy) | 1<br>(very slight) | 2 | 2 | 1<br>(very slight) |
| 6. ROOT: {At Market Maturity} | | | | | |
| Cortex Thickness (Midpoint X-Section) | 0.50 cm | 0.57 cm | 0.72 cm | 0.72 cm | 0.56 cm |
| Core Thickness (Midpoint X-Section) | 1.23 cm | 1.13 cm | 1.16 cm | 0.98 cm | 1.12 cm |
| Carrot Length (Minus Taproot) | 7.78 cm | 9.76 cm | 15.07 cm | 10.64 cm | 9.42 cm |
| Length of Taproot | 11.51 cm | 12.88 cm | 6.66 cm | 5.01 cm | 8.35 cm |
| Diameter at Shoulder | 2.19 cm | 2.23 cm | 2.55 cm | 2.43 cm | 2.17 cm |
| Diameter at Midpoint | 0.59 cm | 1.38 cm | 1.80 cm | 1.93 cm | 1.52 cm |
| Amount Exposed (Above Ground):<br>1 = None; 2 = 1-10%; 3 = 11-20%; 4 = 21-30%; 5 = 31-40%; 6 = >40% | 1 | 1 | 1 | 1 | 1 |
| Shape:<br>1 = Round; 2 = Conic; 3 = Cylindrical | 2 | 2 | 2 | 2 | 2 |
| Collar:<br>1 = Sunken; 2 = Level; 3 = Square | 2 | 2 | 2 | 2 | 2 |
| Shoulder:<br>1 = Rounded; 2 = Sloping; 3 = Square | 1 | 1 | 1 | 1 | 1 |
| Base:<br>1 = Pointed; 2 = Medium; 3 = Blunt | 1 | 1 | 2 | 2 | 1 |
| Surface Smoothness:<br>1 = Very Smooth; 2 = Dimpled or Corrugated | 2 | 2 | 2 | 2 | 2 |
| Number of Secondary Root Scars:<br>1 = None; 2 = Few; 3 = Many | 2 | 2 | 2 | 2 | 2 |
| Appearance of Secondary Root Scars:<br>1 = Not Prominent; 2 = Prominent | 2 | 2 | 2 | 2 | 2 |
| Halo:<br>1 = None; 2 = Faint; 3 = Prominent | 2 | 3 | 3 | 3 | 3 |
| Zoning:<br>1 = None; 2 = Faint; 3 = Prominent | 2 | 3 | 2 | 2 | 3 |
| Flavor Harshness:<br>1 = Very Harsh; Moderately Harsh; 3 = Mildly Harsh | NA | NA | NA | NA | NA |
| Flavor Sweetness:<br>1 = Not Sweet; 2 = Moderately Sweet; 3 = Very Sweet | NA | NA | NA | NA | NA |
| 7. COLORS:<br>Color choices:<br>Name of Color Chart: RHS | | | | | |
| Below Ground Exterior Color | N187A | N187A | N79A | N79B | N79A |
| Shoulder | N187A | N187A | N79A | N79B | N79A |
| Skin | N187A | N187A | N79A | N79B | N79A |
| Cross-Section Interior Color | NA | NA | NA | NA | NA |
| Core | N79A | 6D | 5C | N25C | No color to describe** |
| Cortex | 79A | 79A | 79A | N79A | 79A |
| 8. FLOWER: | NA | NA | NA | NA | NA |
| 9. DISEASE REACTIONS:<br>1 = Susceptible; 2 = Resistant; give races (if known) | NA | NA | NA | NA | NA |
| 10. INSECT REACTIONS:<br>1 = Susceptible; 2 = Resistant; give races (if known) | NA | NA | NA | NA | NA |
| 11. PHYSIOLOGICAL REACTIONS:<br>1 = Susceptible; 2 = Resistant | NA | NA | NA | NA | NA |

TABLE 1-continued

The USDA descriptors for Purple Royale, Anthonina, Purple Elite, Purple Haze, and Deep Purple a field trial. The values are mean values.

| USDA Descriptor | Purple Royale | Anthonina | Purple Elite | Purple Haze | Deep Purple |
|---|---|---|---|---|---|
| Brix<br>1 = Susceptible and 2 = Resistant | NA | NA | NA | NA | NA |
| 12: TOTAL ANTHOCYANIN LEVEL: | 26.26 ppm | 4.01 ppm | 0.97 ppm | 1.53 ppm | 2.93 ppm |

*These are typical values. Values may vary due to environment. Other values that are substantially equivalent are also within the scope of the disclosure. (--- equals not measured).

B. Brix

The degree Brix can be determined in Purple Royale and in the most similar varieties Anthonina, Purple Elite, Purple Haze, and Deep Purple.

The method used was as follows:

C. Total Anthocyanin Level

The anthocyanin level of Purple Royale, Anthonina, Purple Elite, Purple Haze, and Deep Purple was determined using the following protocols:

Anthocyanin Extraction

The skin will be peeled off the root slug and the root will be cut in half in a longitudinal direction. Half of the root will be diced into small pieces. About 1±.0.1 g of the diced root will be weighed in an extraction bag and 5 mL of 0.025 M potassium chloride buffer (pH 1.0) will be added to the bag. Next, the root pieces will be grinded using a pulverizer until chunks are not visible. 1 mL of the juice will be pipetted into a micro centrifuge tube. It will be centrifuged at 10,000×g for 10 minutes at room temperature. The supernatant will be used for anthocyanin analysis.

Total Anthocyanin Measurement Using Spectrophotometer

Cyanidin-3-glucoside will be used as a standard to determine the extinction coefficient of total anthocyanin. The supernatant from purple carrot extraction will be diluted in 0.025M potassium chloride buffer (pH 1.0) and absorbance will be read at 510 and 700 nm using UV-VIS spectrophotometer with a sipper attachment. The anthocyanin concentration will be calculated based on the absorbance level.

A separate trial will be performed to quantitatively determine anthocyanin levels in Purple Royale, Anthonina, Purple Elite, Purple Haze, and Deep Purple using this protocol. Plants will be harvested before bolting started. The recorded anthocyanin levels are the average of about 30 individual roots.

Dry matter (DM) was determined by i) drying an empty aluminum pan in the oven for 1 hour and cool down in a desiccator cabinet; ii) weigh the empty aluminum pan (A=pan wt.); iii) weigh 1±.0.1 g of diced root in the pan (B=pan+fresh root wt.); iv) dry in the convection oven at 100° C. for 24 hours or in the vacuum oven at 90° C. for 18 hours; v) cool in the desiccator cabinet; vi) weigh the pan with the dried root (C=pan+dry root wt.); vii) calculate % dry matter ($\{(C-A)/(B-A)\}*100\%$).

Example 2

Breeding History for Carrot Variety Purple Royale

Years 2014 and 2015—Four different samples of Turkish origin dark purple carrots were provided by Sensient Colors in early 2014 for testing in Livingston, Calif. All subsequent years of production were also grown at the same trial site with essentially the same cultural practices. Based upon previous experience with carrots with an annual growth habit, plots (length=50', bed width=40") of these four lots were planted on 20 Sep. 2014 in the Livingston Research Nursery. Annual carrots typically are best suited for planting and growing during periods of shortening daylength to reduce premature bolting. When daylength begins to rapidly lengthen in the early spring, bolting frequently occurs rapidly and roots convert fleshy tissue into a lignified taproot. Initial observations of these plots noted extremely tall vegetative top growth, highly pubescent leaves, and multiple growing points at the crown. Plots were lifted on 25 Feb. 2015 for steckling selections for potential breeding use. A wide array of root colors and shapes were observed with many forked and split roots and high levels of lenticels. Root colors ranged from a light tan/yellow to violet to extremely dark purple. Intense selection pressure was placed upon selecting a straight, non-forked, smooth root with an Imperator type shape. Roots than met these criteria were further selected for color intensity with the most desirable selections having an almost black coloration across both phloem & xylem. Candidate roots were cut approximately 6" beneath the crown and visually sorted for color content at the tip. Elite roots (ap—proximately 10%) were then laboratory screened for anthocyanin content. Exactly 2 grams of tissue was grated and anthocyanin determined using a proprietary rapid extraction process. Approximately the highest 20% (anthocyanin content) were selected for self-pollination net cages and immediately replanted. The lot designated 'A' had the highest visual levels of pigment and virtually all selections were made therefrom. A total of 28 cages were planted in a fashion where the primary king umbel was enclosed in the cage to create a self-pollination and other umbels were left on the outside to randomly pollinate with other purple/black carrots to create half-sib populations. At bloom, pupae of blue-bottle flies were inserted into these cages for pollination. Four larger cages composed of at least 50 roots/cage were also planted from roots with less extensive selection pressure. All seeds were harvested in mid-July 2015.

Years 2015 and 2016—On Sep. 30, 2015, 24 plots (10'× 40") were planted. Twenty-two were from self-pollinations of elite roots and two were from half-sib populations. Additionally, 0.2 acres were bulk planted from the visually selected large cage 510 and two larger plots (50'×40") with remnant seed of the original seed provided by Sensient Colors. Foliage for plots derived from self-pollination cages was distinctly more compact and consistent than the larger tops exhibited by the original population, the half-sibs, or the less aggressively selected larger cages. Plots were lifted for evaluation and selection on Mar. 17, 2016. Plot number C60212 was identified as having the best combination of a long, straight, smooth root combined with consistent dark pigment, which was further confirmed by laboratory analysis. Most other plots derived from self- or mass-pollinations demonstrated inconsistent root shapes and color segregation ranging from tan/yellow roots to violet to dark purple/black pigment. Altogether, eight individual cages for additional self-pollination and one large cage (10'×20') were replanted on 25 Mar. 2016 for regrowth and seed production. Seed from all cages was harvested in late July 2016.

Years 2016 and 2017—Plots (50'×40") of harvested 2016 seed were planted on 16 Sep. 16, 2016. Growing conditions that winter were extremely challenging. Near record rainfall kept soil moisture at or above saturation and created disease pressure and delayed growth. Stecklings were not lifted until 2 Apr. 2017, which was the latest possible date due to the onset of bolting. Only limited selections were made. Relevant, however, was the anthocyanin test performed comparing the elite cage 668 vs. the original unselected Turkish material. This advanced selection contained 51% higher anthocyanin content than the source population, better overall color uniformity, and more consistent root shape. Overall, four large cages (2 @ 20'×40' and 2 @ 10×20') were planted to increase seed of this elite selection.

Years 2017 and 2018—2 acres of bulk increase of seed from the four 2017 cages was planted on Sep. 26, 2017 to produce stecklings for large scale open multiplication (0.6 acres) that was harvested in July 2018 with a yield of approximately 600 lbs. that was subsequently designated 'Purple Royale'. Photos below provide reference to the visual appearance of selected stecklings and the subsequent 2018 seed production. Steckling photos demonstrate the color uniformity and intensity obtained by selection program as well as improvements in root shape consistency. The current breeding generation is SM3 indicating one generation of self-pollination followed by three generations of mass pollination.

We claim:

1. A plant of carrot variety Purple Royale, wherein representative seed of said carrot variety Purple Royale has been deposited under ATCC Accession No. PTA-127279.

2. A plant part of the plant of claim 1, wherein the plant part comprises at least one cell of the plant.

3. A seed of carrot variety Purple Royale, wherein representative seed of the carrot variety Purple Royale has been deposited under ATCC Accession No. PTA-127279.

4. A method of producing carrot seed, the method comprising crossing the plant of claim 1 with itself or a second carrot plant to produce the carrot seed.

5. The method of claim 4, the method further comprising crossing the plant of carrot variety Purple Royale with a second, non-isogenic carrot plant to produce the carrot seed.

6. A composition comprising the seed of claim 3 comprised in plant seed growth media.

7. The composition of claim 6, wherein the plant seed growth media is soil or a synthetic cultivation medium.

8. A plant of carrot variety Purple Royale further comprising a single locus conversion, wherein said plant otherwise comprises all of the morphological and physiological characteristics of the carrot variety when grown under the same environmental conditions, and wherein representative seed of the carrot variety have been deposited under ATCC Accession No. PTA-127279.

9. A seed that produces the plant of claim 8.

10. The seed of claim 9, wherein the single locus confers a trait selected from the group consisting of increased anthocyanin content, increased flower size, multiple petals, broad environmental adaptation, insect and pest resistance, resistance to bacterial, fungal, or viral disease.

11. The method of claim 5, the method further comprising:
   a. crossing a plant grown from said carrot seed with itself or a different carrot plant to produce seed of a progeny plant of a subsequent generation;
   b. growing a progeny plant of a subsequent generation from said seed of a progeny plant of a subsequent generation and crossing the progeny plant of a subsequent generation with itself or a second plant to produce seed of a progeny plant of a further subsequent generation; and
   c. repeating step (b) with sufficient inbreeding to produce seed of an inbred carrot plant that is derived from the carrot variety Purple Royale.

12. A method of producing a commodity plant product, the method comprising producing the commodity plant product from the plant of claim 1.

13. The method of claim 12, wherein the commodity plant product is anthocyanin.

* * * * *